United States Patent
Berghof et al.

(10) Patent No.: US 7,002,005 B1
(45) Date of Patent: Feb. 21, 2006

(54) **ANALYTICAL DETECTION OF *STAPHYLOCOCCUS AUREUS***

(75) Inventors: Kornelia Berghof, Berlin (DE); Alexander Gasch, Berlin (DE); Charles Mason-Brown, Berlin (DE); Freimut Wilborn, Berlin (DE); Arndt Rolfs, Rostock (DE)

(73) Assignee: Biotecon Diagnostics GmbH, Berlin (DE)

( * ) Notice: Subject to any disclaimer, the term of this patent is extended or adjusted under 35 U.S.C. 154(b) by 0 days.

(21) Appl. No.: 09/463,209

(22) PCT Filed: Jul. 21, 1998

(86) PCT No.: PCT/EP98/04510

§ 371 (c)(1),
(2), (4) Date: May 12, 2000

(87) PCT Pub. No.: WO99/05159

PCT Pub. Date: Feb. 4, 1999

(30) Foreign Application Priority Data

Jul. 21, 1997 (DE) ................................ 197 31 292

(51) Int. Cl.
*C07H 21/04* (2006.01)

(52) U.S. Cl. ................ 536/24.32; 536/23.1; 536/24.3; 435/6; 435/91.2

(58) Field of Classification Search ............... 536/23.1, 536/24.32, 24.3, 24.1; 435/6, 92.1
See application file for complete search history.

(56) References Cited

U.S. PATENT DOCUMENTS

| | | | |
|---|---|---|---|
| 5,370,992 A | * 12/1994 | Shah et al. | 435/6 |
| 5,474,796 A | * 12/1995 | Brennan | 427/2.13 |
| 5,582,975 A | * 12/1996 | Milliman | 435/6 |
| 5,994,066 A | * 11/1999 | Bergeron et al. | 435/6 |
| 6,737,248 B1 | * 5/2004 | Kunsch et al. | 435/69.1 |

FOREIGN PATENT DOCUMENTS

CA 2194411 A1 * 7/1997

OTHER PUBLICATIONS

Green et al. GenBank Accession L36472. Nov. 11, 1994.*
Buchardt et al. Trends in Biotechnology (1993) 11(9): 384-6.*

* cited by examiner

*Primary Examiner*—Juliet C. Switzer
(74) *Attorney, Agent, or Firm*—Frommer Lawrence & Haug LLP; Ronald R. Santucci

(57) ABSTRACT

A kit and a nucleic acid molecule primer and/or probe for the analytical detection of *Staphylococcus aureus* are disclosed. The detection employs nucleic acid amplification and/or nucleic acid hybridization.

12 Claims, No Drawings

ANALYTICAL DETECTION OF STAPHYLOCOCCUS AUREUS

GENERAL BACKGROUND OF THE INVENTION

A bacterium of great clinical relevance is the gram-positive bacterium *Staphylococcus aureus*. It is one of the most frequent causes of nosocomial infections (infections transmitted in hospital), the spread of which is difficult to control because of the occurrence of various forms of antibiotic resistance (for example, resistance to methicillin and vancomycin). *Staphylococcus aureus* is also one of the most frequent causes of food poisoning, which is generally caused by enterotoxins. The frequent occurrence of *Staphylococcus aureus* in foodstuff products therefore requires a regular investigation of potentially contaminated products. Conventional microbiological methods for the detection of *Staphylococcus aureus* are very time-consuming (at least 4 days). There is therefore a great need for alternative methods, by means of which the presence of *Staphylococcus aureus* can be diagnosed rapidly and reliably in the course of the production process (from the raw materials to the finished product).

A number of new methods for routine use in the detection of microorganisms have been developed in recent years. These include immunological methods based on the use of polyvalent or monoclonal antibodies, and methods in which nucleic acid probes are used for detection by means of hybridisation to organism-specific nucleic acids. Further methods described are those based on amplification of a specific nucleic acid, with or without a subsequent confirmation reaction by nucleic acid hybridisation.

Methods used for the amplification of nucleic acids are, for example, polymerase chain reaction (PCR) [U.S. Pat. Nos. 4,683,195; 4,683,202; and 4,965,188], ligase chain reaction [WO Publication 89/09835], "self-sustained sequence replication" [EP 329 822], the "transcription based amplification system" [EP 310 229] and the Qβ RNA-replicase system [U.S. Pat. No. 4,957,858].

The nucleic-acid-based methods mentioned are so sensitive that, unlike in conventional microbiological methods, the tedious process of increasing the quantity of the microorganism to be detected from the sample to be investigated is unnecessary. A test for the presence or absence of the microorganism in question is therefore generally concluded within one working day when using the nucleic-acid-based methods mentioned. This constitutes a considerable time saving, in particular when several days to several weeks are needed for detection by conventional methods.

A number of rapid tests have recently been developed by means of which the presence of *Staphylococcus aureus* can be significantly shortened. These include coagulase tests, various agglutination tests, TNase tests (enzyme activity, monoclonal antibodies), DNA hybridisation tests and PCR tests [for an overview, see BRAKSTAD and MAELAND, (1995), APMIS 103, 209–218]. PCR tests are superior to the other methods in terms of speed and specificity. The PCR tests described hitherto for the specific detection of the *Staphylococcus aureus* species are based on the gene for thermostable nuclease [nuc, Brakstad et al., (1992), J. Clin. Microbiol. 30, 1654–1660] or on a regulator gene essential for methicillin resistance (femA), which is specific for *Staphylococcus aureus* [Ünal et al., (1992), J. Clin. Microbiol. 30, 1685–1691; Vannuffel et al., (1995), J. Clin. Microbiol., 33, 2864–2867]. Using those PCR systems, it has been possible to detect all the investigated species of *Staphylococcus aureus*. It is unclear, however, whether it is also possible to detect coagulase-negative strains of the species *Staphylococcus aureus* using those PCR systems.

The aim of the present invention was to establish a PCR system, the use of which as primers and/or probes ensures as complete detection as possible of all the representatives of the species *Staphylococcus aureus*.

Depending upon the size of the group of microorganisms to be detected and on the evolutionary relationship of microorganisms to be delimited (not to be detected), detection based on differential DNA sequences requires very comprehensive preliminary work in order to find suitable DNA sequences having the desired specificity in each case. The invention described herein relates to DNA sequences by means of which the rapid detection of bacteria of the genus *Staphylococcus*, especially of *Staphylococcus aureus*, is possible.

DESCRIPTION OF THE INVENTION

To detect specific microorganisms by means of nucleic acid hybridisation or amplification, organism-specific oligonucleotides are used. Organism-specific oligonucleotides are nucleic acids, from 10 to 250 bases long (preferably from 15 to 30 bases long), the base sequence of which is characteristic for a specific microorganism or a group of microorganisms. Hybridisation to DNA or amplification of DNA using those organism-specific oligonucleotides (for example as primers or probes) in the above-mentioned methods can be effected, under suitable reaction conditions, only when the DNA of the microorganisms to be detected is present.

Prokaryotic ribosomes generally contain three distinct nucleic acid components, generally known as 5S, 16S and 23S rRNA (ribosomal ribonucleic acid). The genetic information for those ribonucleic acids (rDNA) is typically arranged in the genome in the form of tandems. The typical organisation of such a unit is 16S-23S-5S, the three genes being separated from one another by short hypervariable intergenic regions. A plurality of units are present in the genome, it being possible for the number of repeating units to vary in different bacteria. The high degree of conservation of the DNA sequence in the region of the 16S rDNA, the 23S rDNA and the 5S rDNA throughout the entire bacterial kingdom makes it possible to design non-specific oligonucleotides even without precise knowledge of the DNA sequences of the microorganisms to be investigated. Such non-specific oligonucleotides are characteristic for a relatively large, generally phylogenetically related group of microorganisms. By using those non-specific oligonucleotides, the person skilled in the art will be able, for example following appropriate preliminary tests by DNA amplification by means of PCR, to isolate rDNA fragments, for example of the 23S/5S intergenic region, of any desired microorganism. By DNA sequencing, it is then possible to determine the sequence of the hypervariable intergenic regions of the microorganism in question.

DNA sequencing of the 23S/5S intergenic region of as large as possible a number of bacteria to be detected (for example of various *Staphylococcus* species) on the one hand and a subsequent comparison of those DNA sequences on the other hand make it possible to locate DNA regions that are not modified or are modified only insignificantly in the group under investigation (e.g. all *Staphylococcus* species).

DNA sequencing of the 23S/5S intergenic region of as large as possible a number of bacteria that are not to be detected (for example all bacteria not belonging to the genus *Staphylococcus*) on the one hand and a subsequent comparison of those DNA sequences with the sequence of the bacteria to be detected (e.g. various *Staphylococcus* species) on the other hand make it possible to locate DNA sequences that are characteristic for the bacteria to be detected (e.g. all *Staphylococcus* species). From those DNA sequences it is possible in turn to derive oligonucleotides that can be used as primers and/or probes in nucleic-acid-based methods, with the aim of detecting specifically the group of bacteria in question (e.g. all species of the genus *Staphylococcus*).

The organism-specific oligonucleotides described in the present invention for the detection of bacteria of the genus *Staphylococcus*, especially bacteria of the species *Staphylococcus aureus*, correspond to the 23S/5S intergenic region and the directly adjacent region of the 23S rDNA.

The DNA sequence in that region was determined for a large number of bacteria. Following precise sequence comparisons, organism-specific nucleic acid sequences were determined, from which it is possible to derive primers and/or probes for use in a species- or genus-specific detection method.

The problem underlying the invention is solved according to an embodiment by a nucleic acid molecule that hybridises selectively to RNA or DNA of a group of bacteria of the genus *Staphylococcus*, characterised in that it contains at least 10 successive nucleotides of the region from −113 to +58 relative to the 3'-end of the 23S rDNA of a *Staphylococcus* isolate or their complementary nucleotides. The purpose of the selective hybridisation according to the invention is to detect the mentioned group of bacteria of the genus *Staphylococcus*.

A further embodiment of the invention relates to a nucleic acid molecule that hybridises selectively to RNA or DNA of a group of bacteria of the genus *Staphylococcus*, characterised in that it contains at least 10 successive nucleotides of the region from −113 to +58 relative to the 3'-end of the 23S rDNA of *Staphylococcus aureus* (ATCC 6538) or their complementary nucleotides.

A further embodiment of the invention relates to a nucleic acid molecule that hybridises selectively to RNA or DNA of a group of bacteria of the genus *Staphylococcus*, characterised in that it contains at least 10 successive nucleotides of the region from
(i) nucleotide position 54 to 83 of SEQ ID NO 1, or
(ii) nucleotide position 100 to 166 of SEQ ID NO 1, or
(iii) the sequences complementary to (i) or (ii).

A further embodiment of the invention relates to a nucleic acid molecule for the detection of the presence or absence of bacteria belonging to a group of bacteria of the genus *Staphylococcus*, characterised in that it makes it possible by means of nucleic acid hybridisation and/or nucleic acid amplification methods under suitable reaction conditions to distinguish between bacteria to be detected and bacteria that are not to be detected and that the distinction is possible or is facilitated by a differing nucleic acid sequence at at least one base position in the region of SEQ ID NO: 1, or of its complementary sequence, in the genomic DNA and/or RNA of bacteria to be detected and bacteria that are not to be detected.

A further embodiment of the invention relates to a nucleic acid molecule for the detection of the presence or absence of bacteria belonging to a group of bacteria of the genus *Staphylococcus*, characterised in that it makes it possible by means of nucleic acid hybridisation and/or nucleic acid amplification methods under reaction conditions that are suitable or are known per se to distinguish between bacteria to be detected and bacteria that are not to be detected and that the distinction is possible or is facilitated by a differing nucleic acid sequence at at least one base position in (i) the region 54 to 83 of SEQ ID NO 1, or
(ii) the region 100 to 166 of SEQ ID NO 1, or
(iii) the sequence that is complementary to (i) or (ii) in the genomic DNA and/or RNA of bacteria to be detected and bacteria that are not to be detected.

A further embodiment of the invention relates to a nucleic acid molecule of SEQ ID NO 1 or of its complementary sequence, especially for the detection according to the invention.

A further embodiment of the invention relates to a nucleic acid molecule having a sequence that is shorter than a nucleic acid molecule according to SEQ ID NO 1, namely
(i) a sequence of the region or in the region of the nucleotide positions 54 to 83, or
(ii) a sequence of the region or in the region of the nucleotide positions 100 to 166, or
(iii) a sequence that is complementary to a sequence according to (i) or (ii).

A further embodiment of the invention relates to a nucleic acid molecule having a sequence that is shorter than a nucleic acid molecule according to SEQ ID NO 1, namely
(i) SEQ ID NO 2, or
(ii) SEQ ID NO 3, or
(iii) SEQ ID NO 4, or
(iv) the sequences complementary to (i), (ii) and (iii), respectively.

A further embodiment of the invention relates to a further or different nucleic acid molecule, characterised in that in respect of its sequence in at least 10 successive nucleotides of its nucleotide chain
(i) it is identical to a nucleic acid molecule according to any one of the preceding claims, or
(ii) it corresponds in 9 out of 10 successive nucleotides to a nucleic acid molecule according to any one of the preceding claims, or
(iii) it corresponds in 8 out of 10 successive nucleotides to a nucleic acid molecule according to any one of the preceding claims, or
(iv) it is at least 90% homologous to a nucleic acid molecule according to any one of the preceding claims.

Such a nucleic acid molecule may be characterised in that it is from 10 to 250, preferably from 15 to 30, nucleotides long.

An example of a nucleic acid molecule according to (i) is characterised by SEQ ID NO 5.

A nucleic acid molecule according to the invention may be characterised in that it is single-stranded or double-stranded.

A nucleic acid molecule according to the invention may be characterised in that it is present
(i) as DNA, or
(ii) as RNA corresponding to (i), or
(iii) as PNA (see below), the nucleic acid molecule, where appropriate, being modified in a manner known per se for analytical detection methods, especially methods based on hybridisation and/or amplification.

Such a nucleic acid molecule may be characterised in that the nucleic acid molecule is modified by the replacement of up to 10% of the nucleotides, especially 1 or 2 nucleotides, by analogous components known per se for probes and/or primers, especially by nucleotides that do not occur naturally in bacteria.

A nucleic acid molecule according to the invention may be characterised in that the nucleic acid molecule is modified or labelled or is additionally modified or labelled in that it comprises, in a manner known per se for analytical detection methods, one or more radioactive groups, coloured groups, fluorescent groups, groups for immobilisation on a solid phase and/or groups for an indirect or direct reaction, especially an enzymatic reaction, especially using antibodies, antigens, enzymes and/or substances having an affinity for enzymes or enzyme complexes.

A further embodiment of the invention relates to a kit for analytical detection methods, especially for the detection of bacteria of the genus *Staphylococcus*, characterised by one or more nucleic acid molecules according to the invention.

A further embodiment of the invention relates to a use of one or more nucleic acid molecules according to the invention or of a kit according to the invention for the detection of the presence or absence of bacteria belonging to a group of bacteria of the genus *Staphylococcus*.

That use may be characterised in that the group of bacteria of the genus *Staphylococcus* comprises various strains of *Staphylococcus aureus*.

That use may be characterised in that the group of bacteria of the genus *Staphylococcus* comprises exclusively *Staphylococcus aureus* strains.

Those uses may be characterised in that nucleic acid hybridisation and/or nucleic acid amplification is carried out.

That use may be characterised in that a polymerase chain reaction is carried out as nucleic acid amplification.

Those uses may be characterised in that the detection is carried out by distinguishing between the bacteria to be detected and bacteria that are not to be detected on the basis of differences in the genomic DNA and/or RNA at at least one nucleotide position in the region of a nucleic acid molecule according to the invention.

That use may be characterised in that the distinction is made on the basis of differences in the region of a nucleic acid molecule of SEQ ID NO 1.

To detect the group of microorganisms in question, nucleic acids, preferably genomic DNA, are first released from the cells contained in a sample or bacterial culture to be investigated. By means of nucleic acid hybridisation, the direct detection of organism-specific nucleic acid sequences in the sample to be investigated can then be effected using the organism-specific oligonucleotides according to the invention as probe. Various methods known to the person skilled in the art are suitable for that purpose, such as, for example, "Southern blot" or "dot blot".

Preference is given, however, above all on account of the greater sensitivity, to an indirect detection method in which the DNA/RNA sequences sought are first amplified by means of the above-mentioned methods for the amplification of nucleic acids, preferably PCR.

The amplification of released DNA/RNA using the mentioned methods can be effected using organism-specific oligonucleotides as primers. In that case, specific amplification products are formed only when DNA/RNA of the microorganism to be detected is present. By a subsequent detection reaction using organism-specific oligonucleotides as probes, it is possible to increase the specificity of the detection method. For that subsequent detection reaction it is also possible to use non-organism-specific oligonucleotides as probes.

Alternatively, the nucleic acid amplification may be carried out in the presence of one or more non-specific oligonucleotides, so that possibly also DNA/RNA of other microorganisms that are not to be detected may be amplified. Such an amplification method is generally less specific and should therefore be backed up by a subsequent detection reaction using one or more organism-specific oligonucleotide(s) as probe(s).

Various methods are known to the person skilled in the art by means of which the amplification products that are formed in the indirect methods can be detected. These include, inter alia, visualisation by means of gel electrophoresis, the hybridisation of probes to immobilised reaction products [coupled to nylon or nitrocellulose filters ("Southern blots") or, for example, to beads or microtitre plates] and the hybridisation of the amplification products to immobilised probes (e.g. "reverse dot blots" or beads or microtitre plates coupled with probes).

A large number of different variants have been described by means of which organism-specific oligonucleotides (e.g. probes and primers) can be labelled or modified for the described direct or indirect detection methods. Thus, they may contain, for example, radioactive, coloured or fluorescent groups or groups that have been modified or that modify in some other manner, for example antibodies, antigens, enzymes or other substances having an affinity for enzymes or enzyme complexes. Probes and primers may be either naturally occurring or synthetically produced double-stranded or single-stranded DNA or RNA or modified forms of DNA or RNA, such as, for example, PNA (in those molecules, the sugar units are replaced by amino acids or peptides). Individual nucleotides or several nucleotides of the probes or primers may be replaced by analogous components (such as, for example, nucleotides that do not occur naturally in the target nucleic acid). In the above-mentioned indirect detection methods, detection may also be carried out using an internally labelled amplification product. This can be effected, for example, by the integration of modified nucleoside triphosphates (e.g. coupled to digoxygenin or fluorescein) during the amplification reaction.

Suitable organism-specific oligonucleotides according to the invention are nucleic acids, preferably from 10 to 250 bases long and especially from 15 to 30 bases long, that correspond at least in a 10 base long sequence to the sequences 1 to 5 given below or to their complementary sequences. Relatively small differences (1 or 2 bases) in that 10 base long sequence are possible without loss of the requisite specificity in the amplification and/or hybridisation. The person skilled in the art will know that in the event of such relatively small differences the reaction conditions need to be altered accordingly.

The DNA sequence of *Staphylococcus aureus* (ATCC 6538) in the region of the 23S rDNA (1–113) and of the 23S/5S intergenic region (114–171) is:

(sequence 1 = SEQ ID NO 1)
TTTCCCAACTTCGGTTATAAGATCCCTCAAAGATGATGAGGTTAATAGGTTCGAGGTGG

AAGCATGGTGACATGTGGAGCTGACGAATACTAATCGATCGAAGACTTAATCAAAATAA

ATGTTTTGCGAAGCAAAATCACTTTTACTTACTATCTAGTTTTGAATGTATAA

The sequence in the region of the 23S/5S intergenic region was determined for 8 *Staphylococcus aureus* strains and for at least one representative of each of the following species: *Staphylococcus auricularis, Staphylococcus capitis, Staphylococcus cohnii, Staphylococcus epidermidis, Staphylococcus haemolyticus, Staphylococcus hominis, Staphylococcus saccharolyticus, Staphylococcus saprophyticus, Staphylococcus simulans, Staphylococcus warneri, Staphylococcus xylosus*. The sequence comparisons revealed that the sequences of the different species have a high degree of homology in that region. Three regions having high sequence variability can, however, be detected, namely from nucleotide positions 64 to 73, 110 to 121 and 127 to 156. Oligonucleotides suitable for the detection of bacteria of the genus *Staphylococcus* can therefore be derived from the nucleotide sequences of the different *Staphylococcus* species in the regions 54 to 83 and 100 to 166. For example, from sequence 1 a number of oligonucleotides can be derived that span either fully or partially the variable nucleotide positions 64 to 73, 110 to 121 and 127 to 156 and that are suitable as primers or probes for the selective detection of bacteria of the species *Staphylococcus aureus*.

From sequence 1 there were derived the following oligonucleotides that are especially suitable as primers for the PCR (sequence 2 and sequence 3) and as probes (sequence 4 and sequence 5).

| Oligonucleotide Sa1: | (sequence 2 = SEQ ID NO 2) 5'-GTGGAAGCATGGTGACAT-3' |
|---|---|
| Oligonucleotide Sa2: | (sequence 3 = SEQ ID NO 3) 5'-TAAGTAAAAGTGATTTTGCT TCG-3' |
| Oligonucleotide Sa3: | (sequence 4 = SEQ ID NO 4) 5'-CATTTATTTTGATTAAGTCT-3' |
| Oligonucleotide Sa4: | (sequence 5 = SEQ ID NO 5) 5'-CATTTAAATTTGATTAAGTC-3' |

EXAMPLE 1

Detection of Bacteria of the Species *Staphylococcus aureus* by Polymerase Chain Reaction DNA was isolated from pure cultures of the bacteria listed in Table 1 by means of standard procedures. Approximately from 10 to 100 ng of the DNA preparations were then used in the PCR in the presence of 0.6 µM oligonucleotide Sa1 (SEQ ID NO 2) and 0.6 µM oligonucleotide Sa2 (SEQ ID NO 3), 200 µM dNTP's (N=A/C/G/T mixture; Boehringer Mannheim), 2 mM $MgCl_2$, 16 mM $(NH_4)_2SO_4$, 67 mM Tris/HCl (pH 8.8), 0.01% Tween 20 and 0.03 U/111 Taq-polymerase (Biomaster). The PCR was carried out in a Perkin-Elmer 9600 thermocycler having the following thermoprofile:

| initial denaturing | 94° C. | 3 min |
|---|---|---|
| amplification (35 cycles) | 92° C. | 30 sec |
| | 60° C. | 10 sec |
| final synthesis | 72° C. | 5 min. |

After completion of the PCR reaction, the amplification products were separated by means of agarose gel electrophoresis and visualised by staining with ethidium bromide. The expected product of 94 bp in length was observed only in the cases in which DNA of strains of the species *Staphylococcus aureus* was present (compare Table 1), but not in the presence of DNA of the other tested bacteria. After the end of the run, the DNA contained in the gels was transferred to nylon filters by means of standard methods and was hybridised with an equimolar mixture of the oligonucleotides Sa3 (SEQ ID NO 4) and Sa4 (SEQ ID NO 5) biotinylated at the 5'-end in order to investigate the specificity. Hybridisation was effected in 5×SSC, 2% blocking reagent, 0.1% lauryl sarcosine, 0.02% SDS and 20 pmol/ml of probe for 4 hours at 43° C. Washing was effected in 2×SSC, 0.1% SDS for 1×5 min at room temperature and for 1×5 min at 43° C. Detection was effected according to standard methods by means of alkaline phosphatase conjugates (extravidin, SIGMA, # E-2636) in the presence of 5-bromo-4-chloro-3-indolyl phosphate and 4-nitro-blue tetrazolium chloride (Boehringer Mannheim).

A band was observed on the filters only in the cases in which a band had previously been visible on the agarose gel (see Table 1). Thus, the presence of all the fifty tested *Staphylococcus aureus* strains was detected by means of PCR and by means of hybridisation. Of the total of fifty *Staphylococcus aureus* strains tested, two are coagulase-negative (BioteCon 7030 and BioteCon 7044), which are also detected by the PCR method. On the other hand, none of the tested bacterial strains not belonging to that species was detected using that system.

TABLE 1

Results of the PCR amplification using oligonucleotides Sa1 and Sa2 (SEQ ID NO 2 and SEQ ID NO 3) and subsequent hybridisation using oligonucleotides Sa3/Sa4 (SEQ ID NO 4 and SEQ ID NO 5).

| Species | Designation of strain | PCR | Hybridisation |
|---|---|---|---|
| *Staphylococcus aureus* | ATCC 6538 | + | + |
| *Staphylococcus aureus* | BioteCon 194 | + | + |
| *Staphylococcus aureus* | BioteCon 195 | + | + |
| *Staphylococcus aureus* | BioteCon 196 | + | + |
| *Staphylococcus aureus* | BioteCon 197 | + | + |
| *Staphylococcus aureus* | BioteCon 494 | + | + |
| *Staphylococcus aureus* | BioteCon 514 | + | + |
| *Staphylococcus aureus* | BioteCon 528 | + | + |
| *Staphylococcus aureus* | BioteCon 529 | + | + |
| *Staphylococcus aureus* | BioteCon 530 | + | + |
| *Staphylococcus aureus* | BioteCon 531 | + | + |
| *Staphylococcus aureus* | BioteCon 532 | + | + |

TABLE 1-continued

Results of the PCR amplification using
oligonucleotides Sa1 and Sa2 (SEQ ID NO 2 and SEQ ID NO 3)
and subsequent hybridisation using oligonucleotides Sa3/Sa4
(SEQ ID NO 4 and SEQ ID NO 5).

| Species | Designation of strain | PCR | Hybridisation |
|---|---|---|---|
| Staphylococcus aureus | BioteCon 533 | + | + |
| Staphylococcus aureus | BioteCon 534 | + | + |
| Staphylococcus aureus | BioteCon 535 | + | + |
| Staphylococcus aureus | BioteCon 4286 | + | + |
| Staphylococcus aureus | BioteCon 4287 | + | + |
| Staphylococcus aureus | BioteCon 4288 | + | + |
| Staphylococcus aureus | BioteCon 4289 | + | + |
| Staphylococcus aureus | ATCC 25923 | + | + |
| Staphylococcus aureus | BioteCon 7010 | + | + |
| Staphylococcus aureus | BioteCon 7011 | + | + |
| Staphylococcus aureus | BioteCon 7012 | + | + |
| Staphylococcus aureus | BioteCon 7013 | + | + |
| Staphylococcus aureus | BioteCon 7014 | + | + |
| Staphylococcus aureus | BioteCon 7015 | + | + |
| Staphylococcus aureus | BioteCon 7016 | + | + |
| Staphylococcus aureus | BioteCon 7017 | + | + |
| Staphylococcus aureus | BioteCon 7018 | + | + |
| Staphylococcus aureus | BioteCon 7019 | + | + |
| Staphylococcus aureus | BioteCon 7020 | + | + |
| Staphylococcus aureus | BioteCon 7021 | + | + |
| Staphylococcus aureus | BioteCon 7022 | + | + |
| Staphylococcus aureus | BioteCon 7024 | + | + |
| Staphylococcus aureus | BioteCon 7025 | + | + |
| Staphylococcus aureus | BioteCon 7027 | + | + |
| Staphylococcus aureus | BioteCon 7028 | + | + |
| Staphylococcus aureus | BioteCon 7029 | + | + |
| Staphylococcus aureus | BioteCon 7030 | + | + |
| Staphylococcus aureus | BioteCon 7031 | + | + |
| Staphylococcus aureus | BioteCon 7032 | + | + |
| Staphylococcus aureus | BioteCon 7034 | + | + |
| Staphylococcus aureus | BioteCon 7035 | + | + |
| Staphylococcus aureus | BioteCon 7036 | + | + |
| Staphylococcus aureus | BioteCon 7039 | + | + |
| Staphylococcus aureus | BioteCon 7040 | + | + |
| Staphylococcus aureus | BioteCon 7041 | + | + |
| Staphylococcus aureus | BioteCon 7042 | + | + |
| Staphylococcus aureus | BioteCon 7043 | + | + |
| Staphylococcus aureus | BioteCon 7044 | + | + |
| Staphylococcus arlettae | DSM 20672 | − | − |
| Staphylococcus auricularis | DSM 20609 | − | − |
| Staphylococcus capitis subsp. ureolyticus | BioteCon 2687 | − | − |
| Staphylococcus caprae | DSM 20608 | − | − |
| Staphylococcus carnosus | DSM 20501 | − | − |
| Staphylococcus caseolyticus | DSM 20597 | − | − |
| Staphylococcus chromogenes | DSM 20454 | − | − |
| Staphylococcus cohnii subsp. cohnii, | DSM 20260 | − | − |
| Staphylococcus delphini | DSM 20771 | − | − |
| Staphylococcus epidermidis | BioteCon 515 | − | − |
| Staphylococcus equorum | DSM 20674 | − | − |
| Staphylococcus gallinarum | DSM 20610 | − | − |
| Staphylococcus haemolyticus | BioteCon 2847 | − | − |
| Staphylococcus hominis | DSM 20328 | − | − |
| Staphylococcus hyicus | DSM 20459 | − | − |
| Staphylococcus intermedius | DSM 20373 | − | − |
| Staphylococcus kloosii | DSM 20676 | − | − |
| Staphylococcus lentus | DSM 6672 | − | − |
| Staphylococcus lugdunensis | BioteCon 2681 | − | − |
| Staphylococcus muscae | DSM 7068 | − | − |
| Staphylococcus saccharolyticus | DSM 20359 | − | − |
| Staphylococcus saprophyticus | BioteCon 2685 | − | − |
| Staphylococcus schleiferi subsp. schleiferi | DSM 4808 | − | − |
| Staphylococcus sciuri | DSM 6671 | − | − |
| Staphylococcus simulans | DSM 20322 | − | − |
| Staphylococcus warneri | DSM 20036 | − | − |
| Staphylococcus xylosus | BioteCon 2683 | − | − |
| Bacillus cereus | DSM 31 | − | n.p. |
| Bacillus coagulans | DSM 1 | − | n.p. |
| Bacillus brevis | DSM 30 | − | n.p. |
| Bacillus megaterium | DSM 32 | − | n.p. |
| Bacillus thuringiensis | DSM 350 | − | n.p. |
| Bacillus badius | DSM 23 | − | n.p. |
| Bacillus sphaericus | BioteCon 3136 | − | n.p. |
| Bacillus subtilis | ATCC 6633 | − | n.p. |
| Bacillus circulans | BioteCon 4926 | − | n.p. |
| Bacillus polymyxa | ATCC 8523 | − | n.p. |
| Bacillus mycoides | BioteCon 4928 | − | n.p. |
| Bacillus stearothermophilus | DSM 456 | − | n.p. |
| Pseudomonas aeruginosa | BiotCon 682 | − | n.p. |
| Pseudomonas fluorescens | Biotecon 2439 | − | n.p. |
| Pseudomonas cepacia | BioteCon 672 | − | n.p. |
| Pseudomonas chlororaphis | BioteCon 1753 | − | n.p. |
| Pseudomonas citronellolis | DSM 50332 | − | n.p. |
| Pseudomonas mendocina | DSM 50017 | − | n.p. |
| Pseudomonas pickettii | BioteCon 3323 | − | n.p. |
| Pseudomonas fragi | DSM 3456 | − | n.p. |
| Pseudomonas hydrophila | BioteCon 4883 | − | n.p. |
| Pseudomonas putida | BioteCon 4884 | − | n.p. |
| Pseudomonas oleovorans | DSM 1045 | − | n.p. |
| Pseudomonas pseudoalcaligenes | DSM 50188 | − | n.p. |
| Pseudomonas syringae | DSM 10604 | − | n.p. |
| Pseudomonas mendocina | DSM 50017 | − | n.p. |
| Pseudomonas corrugata | DSM 7228 | − | n.p. |
| Lactobacillus brevis | DSM 1267 | − | n.p. |
| Lactobacillus viridescens | BioteCon 2592 | − | n.p. |
| Lactobacillus kefiranofaciens | DSM 5016 | − | n.p. |
| Lactobacillus lindneri | BioteCon 2599 | − | n.p. |
| Lactobacillus fructivorans | BioteCon 2598 | − | n.p. |
| Lactobacillus casei | DSM 20011 | − | n.p. |
| Lactobacillus vaginalis | DSM 5837 | − | n.p. |
| Lactobacillus fermentum | BioteCon 2597 | − | n.p. |
| Lactobacillus intestinalis | DSM 6629 | − | n.p. |
| Lactobacillus bifermentans | DSM 20003 | − | n.p. |
| Lactobacillus curvatus | DSM 20019 | − | n.p. |
| Lactobacillus coryniformis subsp. torquens | DSM 20004 | − | n.p. |
| Lactobacillus acidophilus | BioteCon 786 | − | n.p. |
| Lactobacillus alimentarius | DSM 20249 | − | n.p. |
| Lactobacillus fructosus | DSM 20349 | − | n.p. |
| Lactobacillus malefermentans | DSM 20177 | − | n.p. |
| Lactobacillus kefir | DSM 20485 | − | n.p. |
| Lactobacillus salivarius subsp. salivarius | DSM 20492 | − | n.p. |
| Lactobacillus homohiochii | DSM 20571 | − | n.p. |
| Lactobacillus sanfrancisco | DSM 20663 | − | n.p. |
| Lactobacillus aviarius | DSM 20655 | − | n.p. |
| Lactobacillus ruminis | DSM 20403 | − | n.p. |
| Leuconostoc mesenteriodes subsp. mesenteriodes | DSM 20240 | − | n.p. |
| Leuconostoc mesenteriodes subsp. dextranicum | DSM 20071 | − | n.p. |
| Leuconostoc mesenteriodes subsp. cremoris | DSM 20346 | − | n.p. |
| Leuconostoc lactis | DSM 20202 | − | n.p. |
| Leuconostoc oenos | DSM 20255 | − | n.p. |
| Leuconostoc gelidum | DSM 5578 | − | n.p. |
| Leuconostoc carnosum | DSM 5576 | − | n.p. |
| Leuconostoc citreum | DSM 20188 | − | n.p. |
| Leuconostoc paramesenteriodes | DSM 20288 | − | n.p. |
| Leuconostoc fallax | DSM 20189 | − | n.p. |
| Leuconostoc pseudomesenteroides | DSM 5625 | − | n.p. |
| Streptococcus downei | DSM 5635 | − | n.p. |
| Streptococcus sp. | DSM 6176 | − | n.p. |
| Streptococcus parauberis | DSM 6631 | − | n.p. |
| Streptococcus gordonii | DSM 6777 | − | n.p. |

TABLE 1-continued

Results of the PCR amplification using
oligonucleotides Sa1 and Sa2 (SEQ ID NO 2 and SEQ ID NO 3)
and subsequent hybridisation using oligonucleotides Sa3/Sa4
(SEQ ID NO 4 and SEQ ID NO 5).

| Species | Designation of strain | PCR | Hybridisation |
|---|---|---|---|
| Streptococcus sp. | DSM 20061 | − | n.p. |
| Streptococcus equinus | DSM 20062 | − | n.p. |
| Streptococcus salivarius subsp. thermophilus | DSM 20259 | − | n.p. |
| Streptococcus canis | DSM 20386 | − | n.p. |
| Streptococcus cricetus | DSM 20562 | − | n.p. |
| Streptococcus anginosus | DSM 20563 | − | n.p. |
| Streptococcus rattus | DSM 20564 | − | n.p. |
| Streptococcus pneumoniae | DSM 20566 | − | n.p. |
| Streptococcus pleomorphus | DSM 20574 | − | n.p. |
| Streptococcus iniae | DSM 20576 | − | n.p. |
| Streptococcus hansenii | DSM 20583 | − | n.p. |
| Streptococcus ferus | DSM 20646 | − | n.p. |
| Streptococcus alactolyticus | DSM 20728 | − | n.p. |
| Streptococcus hyointestinalis | DSM 20770 | − | n.p. |
| Pediococcus parvulus | DSM 20332 | − | n.p. |
| Campylobacter jejuni subsp. jejuni | DSM 4688 | − | n.p. |
| Citrobacter freundii | DSM 30040 | − | n.p. |
| Shigella flexneri | DSM 4782 | − | n.p. |
| Pectinatus cerevisiiphilus | DSM 2834 | − | n.p. |
| Pediococcus inopinatus | DSM 20285 | − | n.p. |
| Proteus mirabilis | BioteCon 4701 | − | n.p. |
| Megasphaera cerevisiae | DSM 20461 | − | n.p. |
| Escherichia coli | BioteCon 4949 | − | n.p. | n.p.: The hybridisation was not performed.

The invention claimed is:

1. A kit for the analytical detection of *Staphylococcus aureus*, comprising at least one nucleic acid molecule primer and/or probe adapted to selectively hybridize to RNA or DNA of *Staphylococcus aureus*, wherein said nucleic acid molecule consists of at least 15 successive nucleotides of SEQ ID NO.1 or sequences complementary to SEQ ID NO.1, wherein said nucleic acid molecule comprises nucleotides 64 to 73 of SEQ ID NO.1, nucleotides 110 to 121 of SEQ ID NO.1, or sequences complementary to said nucleic acid molecules, or wherein said nucleic acid molecule comprises at least 15 successive nucleotides of nucleotides 127 to 156 of SEQ ID NO.1, or sequences complementary to said nucleic acid molecule.

2. The kit of claim 1, wherein said nucleic acid molecule primer and/or probe comprises a sequence selected from the group consisting of SEQ ID NO.2, SEQ ID NO.3, SEQ ID NO.4, or the complementary sequences thereof.

3. The kit according to claim 1, wherein said nucleic acid molecule primer and/or probe is single stranded or double stranded.

4. The kit according to claim 1, wherein said nucleic acid molecule primer and/or probe is DNA, RNA corresponding to said DNA, or PNA.

5. The kit according to claim 1, wherein said nucleic acid molecule primer and/or probe comprises one or more radioactive groups, colored groups, fluorescent groups, groups for immobilization on a solid phase and/or groups for an indirect or direct reaction, and combinations thereof.

6. The kit according to claim 5, wherein said indirect reaction is an enzymatic reaction.

7. The kit according to claim 6, wherein said enzymatic reaction utilizes antibodies, antigens, enzymes and/or substances having an affinity for enzymes or enzyme complexes.

8. The kit according to claim 1, wherein 10% of the sequence of said nucleic acid molecule primer and/or probe is replaced with nucleotides that are not naturally occurring in bacteria.

9. The kit according to claim 1, wherein 1 or 2 nucleotides of said nucleic acid molecule primer and/or probe are replaced with nucleotides that are not naturally occurring in bacteria.

10. An isolated nucleic acid molecule primer and/or probe, consisting of SEQ ID NO.1 or sequences complementary to said nucleic acid molecule.

11. An isolated nucleic acid molecule primer and/or probe, consisting of nucleotide positions 54 to 83 of SEQ ID NO.1 or sequences complementary to said nucleic acid molecule.

12. An isolated nucleic acid molecule primer and/or probe, consisting of a nucleotide sequence selected from the group consisting of SEQ ID NO. 2, SEQ ID NO. 3, SEQ ID NO. 4, and sequences complementary to said nucleic acid molecule.

* * * * *

SEQUENCE LISTING

<160> NUMBER OF SEQ ID NOS: 5

<210> SEQ ID NO 1
<211> LENGTH: 171
<212> TYPE: DNA
<213> ORGANISM: Staphylococcus sp.

<400> SEQUENCE: 1
tttcccaact tcggttataa gatccctcaa agatgatgag gttaataggt tcgaggtgga      60
agcatggtga catgtggagc tgacgaatac taatcgatcg aagacttaat caaaataaat     120
gttttgcgaa gcaaaatcac ttttacttac tatctagttt tgaatgtata a              171

<210> SEQ ID NO 2
<211> LENGTH: 18
<212> TYPE: DNA
<213> ORGANISM: Staphylococcus sp.

<400> SEQUENCE: 2
gtggaagcat ggtgacat                                                    18

<210> SEQ ID NO 3
<211> LENGTH: 23
<212> TYPE: DNA
<213> ORGANISM: Staphylococcus sp.

<400> SEQUENCE: 3
taagtaaaag tgattttgct tcg                                              23

<210> SEQ ID NO 4
<211> LENGTH: 20
<212> TYPE: DNA
<213> ORGANISM: Staphylococcus sp.

<400> SEQUENCE: 4
catttatttt gattaagtct                                                  20

-continued

```
<210> SEQ ID NO 5
<211> LENGTH: 20
<212> TYPE: DNA
<213> ORGANISM: Staphylococcus sp.

<400> SEQUENCE: 5
catttaaatt tgattaagtc                                              20
```